United States Patent [19]

Russell et al.

[11] Patent Number: 4,810,096

[45] Date of Patent: Mar. 7, 1989

[54] PLATE READER

[75] Inventors: Andrew J. Russell, Saffron Walden; Colin Calvert, Bedford, both of England

[73] Assignee: Cambridge Life Sciences, plc, Cambridge, England

[21] Appl. No.: 36,006

[22] Filed: Apr. 8, 1987

[51] Int. Cl.$^4$ ............... G01N 21/01; G01N 21/59
[52] U.S. Cl. ........................ 356/436; 356/400
[58] Field of Search .............. 362/29, 23, 800; 356/436, 440, 443, 444

[56] References Cited

U.S. PATENT DOCUMENTS

| | | | |
|---|---|---|---|
| 3,919,681 | 11/1975 | Nishioka et al. | 362/23 X |
| 3,924,948 | 12/1975 | Thoden et al. | 356/444 X |
| 4,170,950 | 10/1979 | Ozaki | 362/29 X |
| 4,397,560 | 8/1983 | Andresen | 356/440 |
| 4,498,780 | 2/1985 | Banno et al. | 356/440 X |
| 4,596,468 | 6/1986 | Simeth | 356/444 X |

FOREIGN PATENT DOCUMENTS 559983 9/1932 Fed. Rep. of Germany ...... 356/443
WO83/01111 3/1983 PCT Int'l Appl. .

Primary Examiner—Richard A. Rosenberger
Attorney, Agent, or Firm—St. Onge Steward Johnston & Reens

[57] ABSTRACT

A small, compact plate reader is disclosed for microtitre plates. The reader comprises a totally enclosed housing (19), means e.g. a drawer (2) for receiving and inserting into the housing a microtitre plate (7) which is received into the housing between a light source and a photodetector positioned in vertical alignment above and below the microtitre plate. The light source and detector are mounted on a carriage movable in the housing along each of two orthogonal axes by means of the manual control knobs (10,11) on either side of the housing. The light source and detector are thus positionable with each of the wells of the microtitre plate in turn enabling absorbancy measurements to be made, and visually displayed by a digital display (9). A window (8) in the housing (1) marked with indices corresponding to the cells in the microtitre plate permits a visual indication of the position of the detector head relative to the microtitre plate, for example, by illumination from below of the appropriate index mark by the light source itself, or by a secondary light source.

18 Claims, 2 Drawing Sheets

PLATE READER

This invention relates to plate readers for microtitre plates, more particularly plate readers for measuring the absorbance of samples, usually liquid samples, contained within the wells of a microtitre plate.

A wide variety of plate readers is known involving various degrees of sophistication and embodying a wide variety of technical features. Included amongst such prior art there may be mentioned, for example, the devices described in International Applications Nos. WO 82/00361 and WO 82/00365, those described in European Published Applications Nos. 0 012 698, 0 108 524 and 0 136 002, and those in U.S. Pat. No. 4,115,101 and U.S. Pat. No. 3,627,431.

In contrast to the foregoing, the present invention seeks to provide a simple, robust plate reader, which is inexpensive, easy to use, accurate and highly portable.

In accordance with the invention, such a plate reader comprises a totally enclosed housing, plate supporting means within said housing for receiving and supporting in a horizontal position a microtitre plate containing in its wells samples the absorbance of which is to be measured by the plate reader, means in said housing providing access to said plate supporting means for the placement thereon and removal therefrom of said microtitre plate, a carriage movably mounted in the housing and carrying in spaced vertical alignment a light source and a light detector, said source and detector being positioned one above and one below the plane of the microtitre plate when in position on said support means, means for moving the carriage within the housing so as to selectively position said source and said detector in vertical alignment in turn with each of the wells of said microtitre plate, each of said wells in turn being positioned between the light source and the detector, indicator means attached to the carriage and visible externally of the housing to indicate the positioning of the light source and the detector relative to the wells of the microtitre plate, means for measuring the amount of light transmitted from the light source to the detector through each of the wells in turn, and means for indicating and/or recording the absorbance of the samples contained within those wells.

A particular advantage arising from the fact that, in the plate reader of this invention, the microtitre plate is held in a fixed position, whilst the light source and detector are moved thereover from well to well, is in the over-all dimensions of the reader which can be kept quite small to provide a neat, compact, easily portable unit which may carry its own power pack and/or be adapted for connection to an outside power source. Also, the concept of a totally enclosed housing into which the microtitre plate can be inserted means that extraneous light sources, which might otherwise affect the absorbancy readings, can be totally excluded. Indeed, in one embodiment, the microtitre plate can be inserted into a compartment within the housing which is completely light proof, and in which the only source of light is that which is used to make the absorbancy measurement.

In a preferred arrangement the plate supporting means are located in a drawer member slidably mounted in the housing, and which can be opened to insert (or remove) the plate, and closed to bring the plate into position inside the housing between the light source and the detector.

As indicated the light source and the detector are mounted on a movable carriage inside the housing one above the other in vertical, spaced alignment. Usually, but not necessarily, the light source will be in the upper position so that, when the microtitre plate is in position, the light beam passes downwardly through the sample and onto the detector. Since the wells on the conventional microtitre plate are usually laid out on a rectangular grid pattern, the carriage, in the preferred embodiment, is constrained to move within the housing along two axes at right angles to each other, and manually operable means are provided externally of the housing for moving the carriage independently along each axis, so that the light source and the detector can be brought into vertical alignment with each of the wells of the microtitre plate in turn.

A variety of different mechanisms can be used to move the carriage but most conveniently the carriage can be mounted in appropriate slides within the housing, and moved therealong by, for example, a rack and pinion mechanism, or a lead screw, or a combination of the two. In one particular arrangement the carriage is constructed in two parts, the one being slidably mounted in the housing and constrained to move along one of the two axes at right angles, and the other part being slidably mounted on the first part and constrained to slide thereon along the other of the two axes.

In order to provide positive location of the carriage at each of the locations whereat the light source and detector are in correct vertical alignment with the well containing the particular sample to be measured at that moment, biassed detent means are preferably provided, e.g. one or more spring loaded ball detents, which serve to hold the carriage in a particular position whilst the measurement is made.

In order to provide the user with a visual indication of the position of the carriage relative to the microtitre plate, a window is preferably provided in the housing through which a position indicating means carried by the carriage is visible. This position indicating means can, in one embodiment, be the light source itself, or, in an alternative embodiment, can be a separate light source, for example, a light emitting diode LED, mounted on the carriage and visible through the window. Alternatively, it can simply be a luminescent or non-luminescent marker carried by the carriage and visible through the window.

Most conveniently the window is positioned in the housing in a plane parallel with and directly above the microtitre plate, when in position to the housing, the window being marked, e.g. numerically, or provided in some other way with markings corresponding to the identifying numerals of the wells of the microtitre plate, the position of the indicator means relative to those markings thus corresponding to and identifying each well in turn as the measuring head comprising the light source and the detector is brought into registration therewith. Preferably the window is appropriately coloured, e.g. red, to reduce or eliminate those wavelengths of incident light which might otherwise interfere with the absorbance measurements.

Other advantageous features of plate readers according to this invention will be apparent from the following detailed description of a preferred embodiment presented by way of illustration and described with reference to the accompanying drawings, in which.

Figure 1:
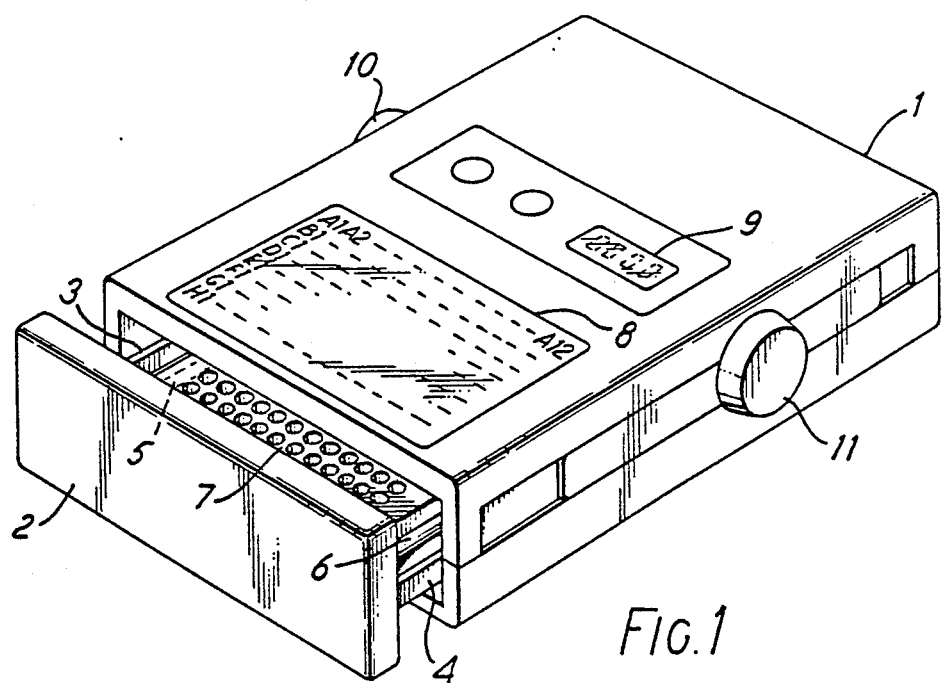
FIG. 1 is a general perspective view of the plate reader with the plate receiving drawer slightly open.

Referring to FIG. 1, the plate reader comprises a generally flat, rectangular housing (1) having a plate receiving drawer (2) slidably mounted in one end of the housing on rails (3, 4). Mounted in the drawer are two elongated support rails (5, 6) extending into the housing, and which provide a seating for a conventional 96 well microtitre plate (7), although, of course, the reader may be adapted for use with microtitre plates of other sizes.

When inserted onto its seating, and with the drawer closed, the microtitre plate (7) is located immediately below a window (8) in the upper surface of the housing (1), the window being suitably coloured, e.g. red, to filter out wavelengths of incident light which might otherwise interfere with the absorbancy readings. As indicated in FIG. 1, the window is suitably marked with indices A1, A1 ... B1, B1 ... etc. through to H11, H12, corresponding in position to the numbered wells of the microtitre plate (7).

Also located in the upper surface of the housing (1) is a digital display panel (9) which when the plate reader is in use displays digital values corresponding to the measured absorbancy of the samples contained within the wells A1 to H12 of the microtitre plate (7). Also located adjacent the display panel (9) are ON and OFF buttons for the user to switch the plate reader on and off.

Located to either side of the housing (1) are two control knobs (10, 11) which serve to move the reading head inside the plate reader into position relative to each of the wells in turn of the microtitre plate. The mechanism by which this is achieved is illustrated somewhat diagrammatically by FIG. 2.

Figure 2:
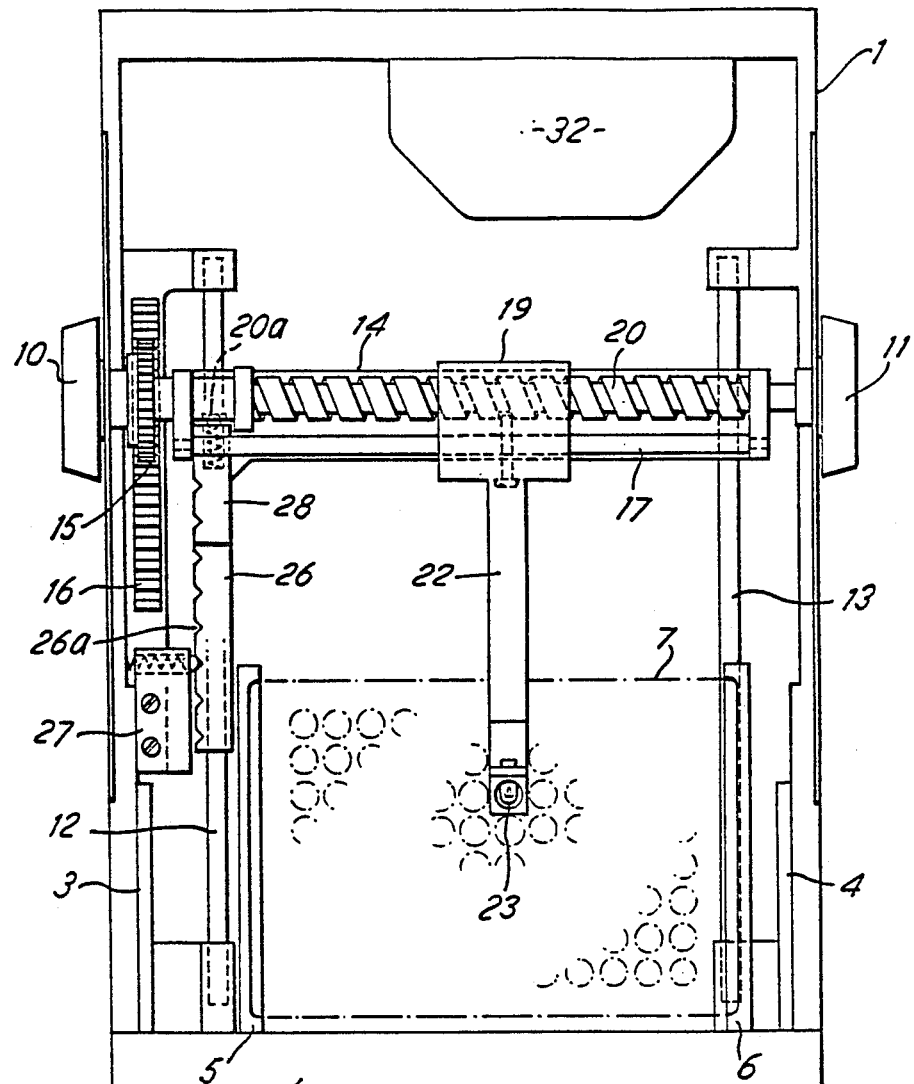
FIG. 2 is a diagrammatic plan view of the inside of the plate reader with the cover removed and showing the mechanical operation of the reader.

In FIG. 2, the upper half or cover of the housing (1) has been removed to reveal the mechanically operative parts of the plate reader. Mounted in the lower half of the housing (1) are two parallel slide rails (12, 13) which slidably carry an elongated carriage member (14) essentially spanning the width of the inside of the housing (1). The carriage member (14) can be made to travel lengthwise of the housing along the rails (12, 13) by means of the left hand control knob (10) which drives a pinion (15) rotatably mounted on the carriage (14) and engaging a rack (16) secured in the base of the housing (1) parallel with the rails (12, 13).

Figure 3:
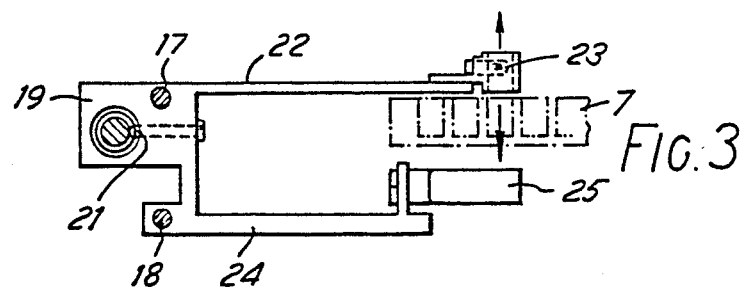
FIG. 3 is a side elevation of the reading head used in the reader.

The carriage member (14) extending transversely of the housing (1) comprises upper and lower slide rails (17, 18) extending longitudinally of the carriage member, i.e. transversely of the housing, and upon which is slidably mounted a bifurcated reading head (19) shown in more detail in FIG. 3.

The reading head (19) can be made to travel transversely of the housing along the slide rails (17, 18) by means of the right hand control knob (11) which drives a lead screw (20) rotatably mounted on the carriage (14) and extending along the length of the carriage parallel with the rails (17, 18). A spring loaded ball follower (21) is mounted in the reading head (19) to engage in the track of the lead screw (20).

As will be apparent from the description so far, the two control knobs (10, 11) operate to move the reading head (19) along two orthogonal axes within the housing, knob (10) controlling longitudinal movement, and knob (11) controlling the transverse movement. In this way the reading head can be moved into correct alignment with each of the wells in turn of the microtitre plate, thus permitting the absorbancy measurements to be made on each of those wells.

As will be seen from FIG. 3, the reading head (19) is a bifurcated structure comprising an elongated upper arm (22) extending above the microtitre plate and carrying at its distal end a light source (23), e.g. a miniature filament bulb, and an elongated, parallel lower arm (24) extending below the microtitre plate and carrying at its distal end a photodetector cell (25). The relative positions of the source and the detector can, of course, be reversed, and will, of course, be in vertical alignment one with the other, thereby to permit absorbancy measurements to be made on each of the wells in turn.

In the currently preferred embodiment, the light source (23) is in the upper position so that the light therefrom not only passes through the sample onto the detector, but either directly or through back scattering, also illuminates the appropriate one of the indices A1 to H12 on the window (8) in the upper surface of the housing (1) i.e. the index corresponding to the particular well of the microtitre plate, which at that moment is positioned between the source and the detector. In that way the user is able to position the light source and detector accurately with respect to each well in turn, thereby enabling the absorbancy to be measured and displayed on the digital display (9).

To assist still further in the accurate positioning of the light source and detector above and below, respectively, each of the wells of the microtitre plate, two ball detent mechanisms are provided to provide positive location of the reading head at each of the 96 positions corresponding to the 96 wells of the microtitre plate. To this end, the carriage member (14) has a forwardly extending arm (26) parallel with the slide rail (12) and which has eight notches (26a), corresponding to the eight rows of wells A to H in the microtitre plate, and which are engaged in turn by a spring loaded ball detent (27) mounted inside the lower half of the housing (1). This provides positive location of the reading head at each of the eight positions along its first axis of movement. To provide positive location of the reading head at each of the twelve positions along the other axis, corresponding to the columns 1 to 12 of the microtitre plate, a second spring loaded ball detent (28) is mounted on the carriage (14) and engages a notch or recess (20a) on the surface of the lead screw (20), and the pitch of the lead screw is selected so that one complete revolution of the lead screw moves the reading head exactly from one column to the next, the detent (28) engaging the recess (20a) on the lead screw once on each revolution, thereby positively locating the reading head at each of the columns 1 to 12 in turn. Of course, different ratios may be used, e.g. with two diametrically opposed detent recesses on the lead screw, the pitch of the screw will be such that one half revolution of the screw will be sufficient to move the reading head from one column to the next.

Figure 4:
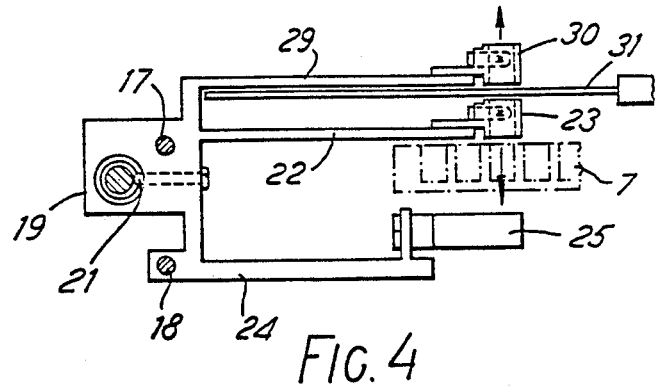
FIG. 4 is a side elevation of an alternative reading head, for use in an alternative embodiment of the plate reader and in which an additional lightproof screen is provided inside the housing to shield the plate completely from extraneous light during the measurement process.

In the modification illustrated by FIG. 4, the reading head has three arms rather than two, the extra arm (29)

carrying at its distal end a separate light source (30) in vertical alignment with the absorbancy light source (23) and the detector (25), and which illuminates the indices on the window (8). This modification permits the interpositioning of a lightproof screen (31) mounted in the housing and extending between the arms 22 and 29, thus screening the microtitre plate totally from all extraneous light sources.

As will be apparent from the foregoing description, the plate reader of this invention is extremely compact, inexpensive and simple to operate. It may be provided with its own power pack, for example, a rechargeable battery or batteries (32) mounted in the housing, and/or it can be provided with an external power source.

The electrical circuitry required to measure the absorbancy of the samples contained in the wells of the microtitre plate, and to display the measured values on the digital display, is perfectly conventional, and well within the capability of the person skilled in the art. Conveniently the circuitry can be mounted on a circuit board positioned in the upper half or cover of the housing. Depending on the degree of sophistication required, the circuitry may or may not incorporate a memory to store absorbancy readings for subsequent display or read out. These and other modifications, variations and refinements are all well within the skill of the person skilled in the art and may be practiced without departing from the scope of this invention, which resides essentially in the mechanical and physical attributes of the plate reader and as defined by the appended claims.

We claim:

1. A plate reader for microtitre plates, comprising a totally enclosed housing, plate supporting means within said housing for receiving and supporting in a horizontal position a microtitre plate containing in its wells samples the absorbance of which is to be measured by the plate reader, means in said housing providing access to said plate supporting means for the placement thereon and removal therefrom of said microtitre plate, a carriage movably mounted in the housing and carrying in spaced vertical alignment a light source and a light detector, said source and detector being positioned one above and one below the plane of the microtitre plate when in position on said support means, means for moving the carriage within the housing to as to selectively position said source and said detector in vertical alignment in turn with each of the wells of said microtitre plate, each of said wells in turn being positioned between the light source and the detector, indicator means attached to the carriage and visible externally of the housing to indicate the positioning of the light source and the detector relative to the wells of the microtitre plate, means for measuring the amount of light transmitted from the light source to the detector through each of the wells in turn, and means for indicating and/or recording the absorbance of the samples contained within those wells.

2. A plate reader according to claim 1, wherein the carriage is constrained within the housing to move along two axes at right angles at one to the other, and means are provided to move the carriage independently along each of those axes thereby to bring the light source and detector into vertical alignment in turn with each of the wells of the microtiter plate.

3. A plate reader according to claim 2, wherein said carriage is constructed in two parts, one constrained to move within said housing along one of said axes, and the other being movably mounted on the first and constrained to move thereonalong the other of said two axes.

4. A plate reader according to claim 1, wherein the means for providing access to the interior of the housing for the placement and removal of the microtitre plate comprise a drawer slidably mounted in the housing and wherein is located said plate supporting means whereby, when the drawer is open the microtitre plate can be placed therein or removed, and when the drawer is closed the plate is supported in a horizontal plane between the light source and the light detector.

5. A plate reader according to claim 3, wherein biassed detent means are provided to locate the carriage positively at each position within the housing whereat the said light source and detector are in vertical alignment with each in turn of said wells of said microtitre plate.

6. A plate reader according to claim 1, wherein said indicator means comprise a translucent window in the housing, through which a position indicating means attached to the carrier is visible thereby to indicate the position of the light source and the detector relative to the wells in the microtitre plate.

7. A plate reader according to claim 6, wherein the position indicating means is the light source itself.

8. A plate reader according to claim 1, wherein the plate supporting means, the light source and the light detector are located within a substantially completely lightproof compartment within said housing.

9. A plate reader according to claim 8, wherein the position indicating means comprise a second light source mounted on said carriage, but positioned externally of said lightproof compartment so as to be visible through a translucent window in the housing.

10. A plate reader according to claim 6, wherein said window is located in said housing in a plane located above and parallel with the microtitre plate, when in position therein, said window having markings thereon or associated therewith which, at any given position of the carriage, identify the particular well which, at that moment, is located between the light source and the detector.

11. A plate reader according to claim 1, wherein the absorbance indicating and/or recording means comprise a digital display indicating the absorbances of the samples under test and contained within the wells of the microtitre plate.

12. In a plate reader for microtitre plates of the type comprising an enclosed housing, means for receiving a microtitre plate within the housing in a position to be scanned by a reading head movable relative to the plate to bring said head into alignment with each of the wells of the microtitre plate in turn, illuminating means associated with said reading head for directing a beam of light through each of said wells in turn, and measuring means for measuring the amount of light transmitted by each of said wells in turn, the combination of improvements comprising:
a substantially flat housing means having in its upper surface a window marked with an identifying grid enabling the identification of the individual wells of the microtitre plate when received within the housing;
a drawer slidably mounted in the housing means and slidable with respect thereto between an open position, thereby to permit the insertion therein and subsequent removal therefrom of a microtitre plate to be held therein in a fixed position by plate supporting means, and a closed position in which said plate is located totally within the housing means in a fixed position relative thereto in alignment with, and in a horizontal plane parallel to, but vertically spaced from and below said window;

a carriage means mounted in said housing means and manually movable thereon along two orthogonal axes at right angles one to the other by manually operable control means mounted externally of the housing, said carriage means comprising two parallel, vertically spaced apart arms lying in two parallel planes located above and below, respectively, the horizontal plane occupied by said microtitre plate when in position in the housing, said arms carrying at their distal ends, respectively, a light source and, vertically aligned therewith, a light detector means for detecting and measuring light transmitted through a respective one of the wells of the microtitre plate, when said light source and detector means are positioned in vertical alignment with said well, one immediately thereabove and the other immediately therebelow;

manually operable control means mounted externally of the housing and operably connected internally of the housing to said carriage and operable to move said carriage relative to the housing and said plate along said two orthogonal axes thereby to bring said light source and said detector means into vertical alignment with each of said wells in turn;

detent means for positively locating the carriage within said housing when said light source and detector means are in vertical alignment with each in turn of said wells; and a position indicating means carried by the carriage and visible through said window to indicate the instantaneous position of the carriage inside the housing and to identify the particular well which, at that moment, is located between the light source and the detector and whose transmittance or adsorbance is to be measured.

13. A plate reader according to claim 12, wherein said light source is carried by the uppermost of said two vertically spaced apart arms and is visible through said window to provide said position indicating means.

14. In a plate reader according to claim 12, the further improvement comprising a lightproof baffle positioned in said housing and lying in a horizontal plane between said window and said microtitre plate when inserted in the housing, thereby to define within the housing a totally lightproof compartment for the microtitre plate.

15. A plate reader according to claim 14, wherein the position indicating means comprises a third arm on said carriage means parallel with but vertically spaced above the uppermost of said two arms carrying said light source and detector means respectively, said third arm lying in a horizontal plane between said window and said lightproof baffle and carrying at its distal end an indicator means vertically aligned with said light source and said detector means and visible through said window to indicate the position of the carriage and identify the particular well which at that moment lies between the light source and the detector means.

16. A plate reader according to claim 15, wherein said indicator means comprises a second light source carried on the distal end of said third arm and visible through said window, but shelded from the microtitre plate when in position in the housing by said lightproof baffle.

17. In a plate reader for microtitre plates of the type comprising an enclosed housing, means for receiving a microtitre plate within the housing in a position to be scanned by a reading head movable relative to the plate to bring said head into alignment with each of the wells of the microtitre plate in turn, illuminating means associated with said reading head for directing a beam of light through each of said wells in turn, and measuring means for measuring the amount of light transmitted by each of said wells in turn, the combination of improvements comprising:

a substantially flat housing means;

a drawer slidably mounted in the housing means and slidable with respect therein between an open position, thereby to permit the insertion therein and subsequent removal therefrom of a microtitre plate to be held therein in a fixed position by plate supporting means, and a closed position in which said plate is located totally within the housing means in a fixed horizontal plane;

a carriage means mounted in said housing means and manually movable thereon along two orthogonal axes at right angles one to the other by manually operable control means mounted externally of the housing, said carriage means comprising two parallel, vertically spaced apart arms lying in two parallel planes located above and below, respectively, the horizontal plane occupied by said microtitre plate when in position in the housing, said arms carrying at their distal ends, respectively, a light source and, vertically aligned therewith, a light detector means for detecting and measuring light transmitted through a respective one of the wells of the microtitre plate, when said light source and detector means are positioned in vertical alignment with said well, one immediately thereabove and the other immediately therebelow;

manually operable control means mounted externally of the housing and operably connected internally of the housing to said carriage and operable to move said carriage relative to the housing and said plate along said two orthogonal axes thereby to bring said light source and said detector means into vertical alignment with each of said wells in turn;

detent means for positively locating the carriage within said housing when said light source and detector means are in vertical alignment with each in turn of said wells; and a position indicating means to indicate the instantaneous position of the carriage inside the housing and to identify the particular well which, at that moment, is located between the light source and the detector and whose transmittance or adsorbance is to be measured.

18. A plate reader according to claim 17, wherein the substantially flat housing means has a window in its upper surface marked with an identifying grid enabling the identification of the individual wells of the microtitre plate which is received in said housing means in a fixed position immediately below and in alignment with said window, and wherein the position indicating means comprise an indicator means carried by the carriage and visible through said window to indicate the instantaneous position of the carriage inside the housing and to identify by reference to said grid the particular well which, at that moment, is located between the light source and the detector and whose transmittance or adsorbance is to be measured.

* * * * *